United States Patent [19]

Fong et al.

[11] Patent Number: 4,957,893
[45] Date of Patent: Sep. 18, 1990

[54] CATALYST FOR MAKING AMINES FROM ALCOHOLS

[75] Inventors: Pak Y. Fong; Kim R. Smith; Joe D. Sauer, all of Baton Rouge, La.

[73] Assignee: Ethyl Corporation, Richmond, Va.

[21] Appl. No.: 365,213

[22] Filed: Jun. 12, 1989

Related U.S. Application Data

[60] Division of Ser. No. 133,733, Dec. 16, 1987, which is a continuation-in-part of Ser. No. 22,095, Mar. 5, 1987, abandoned, which is a continuation-in-part of Ser. No. 22,047, Mar. 5, 1987, abandoned, which is a continuation-in-part of Ser. No. 79,522, Jul. 30, 1987, abandoned.

[51] Int. Cl.$^5$ .................. B01J 23/02; B01J 23/06; B01J 23/72; B01J 27/232
[52] U.S. Cl. .................................. 502/174; 502/343
[58] Field of Search .................. 502/174, 342, 343

[56] References Cited

U.S. PATENT DOCUMENTS

| 3,546,140 | 12/1970 | Gutmann et al. | 502/343 X |
| 3,961,037 | 6/1976 | Davies et al. | 502/342 X |
| 4,111,847 | 9/1978 | Stiles | 502/342 |

Primary Examiner—W. J. Shine
Attorney, Agent, or Firm—Joseph D. Odenweller; Patricia J. Hogan

[57] ABSTRACT

Mono- and di-lower alkylamines, e.g. methylamine or dimethylamine, are alkylated by reaction with $C_{8-22}$ alcohol in the presence of hydrogen at a temperature of about 105°–275° C. in contact with a copper-zinc-alkaline earth metal base containing catalyst (e.g., CuO—ZnO—Ba(OH)$_2$) while removing water formed in the reaction.

12 Claims, No Drawings

CATALYST FOR MAKING AMINES FROM ALCOHOLS

This application is a division of application Ser. No. 133,733, filed Dec. 16, 1987, which in turn is a continuation-in-part of applications Ser. No. 022,095 which in turn is a continuation-in-part of Ser. No. 022,047 both filed Mar. 5, 1987, both now abandoned, which is a continuation-in-part of Ser. No. 079,522 filed Jul. 30, 1987, now abandoned.

BACKGROUND

It has long been known that alcohol can react with ammonia or primary or secondary amines to replace one or more hydrogen atoms bonded to nitrogen with the alkyl residue of the alcohol. The reaction is promoted by catalysts. Use of a supported oxygen compound of phosphorus is reported in U.S. Pat. No. 2,073,671. Another process is described in U.S. Pat. No. 2,160,058 using copper-barium-chromium oxides, copper-chromium oxides or copper-aluminum oxides. Reaction of ethylene glycol with ammonia using a catalyst such as nickel-aluminum, nickel-silicon, nickel, copper, copper-chromium, copper-zinc-chromium, thorium, magnesium, molybdenum or osmium oxides is said to form alkoxy amines according to U.S. Pat. No. 2,160,058. Reaction of an alcohol with ammonia or an amine in the presence of hydrogen using an alumina or silica supported cobalt-nickel-copper-catalyst is described in U.S. Pat. No. 4,014,933. Hoshino et al. U.S. Pat. No. 4,210,605 describe a process for making aliphatic amines by reacting an aliphatic alcohol or aldehyde with ammonia or a primary or secondary amine using a homogenous colloidal catalyst formed by dissolving a copper or silver salt of a fatty acid in alcohol and reducing the metal. Optionally the solution can contain a Group VIII metal carboxylate or a manganese or zinc metal carboxylate. It can also contain an alkali metal or alkaline earth metal carboxylate. The catalyst formed is a homogenous colloid that cannot be separated by filtration. In contrast the present catalyst is a solid catalyst that can be removed by filtration and recycled.

More recently, U.S. Pat. No. 4,409,399 describes the alkylation of ammonia or a primary or secondary amine using as the catalyst an unsupported copper oxide or hydroxide-nickel oxide or hydroxide and optionally a Group II metal oxide or hydroxide.

One of the problems encountered when making long-chain alkyl di-lower alkylamines such as $C_{8-22}$ alkyl dimethylamines by the reaction of a long-chain alcohol with a di-lower alkylamine is that any unreacted long-chain alcohol remaining in the reaction mixture will boil at about the same temperature as the desired product which makes purification very difficult. Hence, it is essential that conversion of alcohol be essentially complete, e.g., at least 95%, to have a commercially viable process when making an amine such as a $C_{8-22}$ alkyl dimethylamine. Likewise it is essential that disproportionation to form long-chain alkylamine and/or long-chain alkyl mono-lower alkylamine be minimized as these primary and secondary amines are also extremely difficult to separate from the desired long-chain alkyl di-lower alkylamine product.

SUMMARY OF THE INVENTION

It has now been discovered that both mono- and di-lower alkylamines can be alkylated in high yields by reaction with an alcohol in the liquid phase and in contact with a supported or unsupported catalyst which initially consists essentially of copper or copper oxide, zinc or zinc oxide and an alkaline earth metal base. The catalyst can optionally include cobalt, chromium and/or nickel. Introduction of hydrogen during at least part of the reaction increases the alkylation rate.

DESCRIPTION OF THE PREFERRED EMBODIMENTS

A preferred embodiment of the invention is a process for alkylating an amine by reacting a mono- or di-lower alkylamine with an alcohol in the liquid phase at a temperature of about 100°–300 °C. and in contact with a non-colloidal catalyst consisting essentially of (1) copper and/or copper oxide, (2) zinc or zinc oxide and (3) an alkaline earth metal compound.

The process can be conducted by forming a mixture of the alcohol and an alkylamine or dialkylamine containing the catalyst and stirring the mixture at reaction temperature, optionally but preferably while contacting the mixture with hydrogen. In practice the hydrogen can be sparged into the liquid phase and the off-gas, consisting mainly of hydrogen, passed through a condenser to condense water and other volatiles which co-distill. The hydrogen can then if desired be recirculated to the reaction mixture. Any amine or alcohol lost in the vent stream can be made-up by adding additional alcohol or amine.

The reaction temperature can vary widely. The temperature should be high enough to cause the reaction to proceed at a reasonable rate but not so high as to cause decomposition of reactants or products. A useful temperature range in which to experiment is about 100°–300 °C. A preferred temperature is 150°–275 °C. A more preferred temperature range is about 180°–250° C. Excellent results have been achieved in the range of 190°–230 °C.

The reaction can be conducted at atmospheric pressure or above or below atmospheric pressure. Best results have been achieved operating at atmospheric pressure. However, if pressure is required to reach the desired alkylation temperature or to increase the amount of amine in the reaction mixture, then such pressure can be applied. When operating under pressure it is still preferred to sparge hydrogen through the liquid phase and to vent the vapor phase through a pressure regulating valve.

The ratio of alcohol to amine can vary over a wide range. Stoichiometry for $C_{8-22}$ alkyl dimethylamine requires one mole of alcohol per each mole of dialkylamine. In practice an excess of amine can be used. Any unreacted amine can be later removed by distillation. When using a higher alcohol and a lower dialkyl amine such as dimethylamine, it is preferred to have the amine in large excess so that all or almost all of the alcohol is consumed. This is because the higher alcohols are very difficult to separate from the higher alkyl di-lower alkylamines. A useful range is about 1.1–20 moles of di-lower alkylamine per mole of higher (e.g. $C_{8-22}$) alcohol. In practice the di-lower alkylamine in the vapor phase, preferably in combination with hydrogen, is continuously injected into the heated liquid reaction mixture. The di-lower alkylamine that does not react with the alcohol can be recovered from the vent gas and reinjected until substantially all (e.g., at least 95 percent) of the alcohol is converted.

When making a di-($C_{8-22}$ alkyl) methylamine the ratio of all or almost all of the initial alkyl amine. An efficient way to conduct the process is to feed mono-alkyl amine until the mole ratio of alcohol to amine feed is about 1.8–2.5:1. The mono-alkyl amine addition can be discontinued and one can proceed to monitor the reaction composition using gas chromatography (GC) as the reaction proceeds. If it is seen that the alcohol is consumed while substantial amounts of mono- and/or di-alkyl amile remain, then more alcohol can be added to convert the mono- and/or di-alkyl amine to tri-alkyl amine. If on the other hand the amines in the reaction mixture are all or almost all tri-alkyl amines while unreacted alcohol remains, then additional mono-alkyl amine can be added to react with this alcohol. The stoichiometric ratio for the reaction is 2 moles of alcohol per mole of alkyl amine but the amount of alcohol and amine actually fed or added to the reaction may vary somewhat from this ideal ratio due to factors such as mono-alkyl amine being lost in the vent gas.

The reaction is conducted for a period of time adequate to achieve the desired degree of alkylation. The reaction is usually complete in about 1–24 hours. A preferred reaction time is about 2–12 hours. Under the most preferred reaction conditions the reaction is essentially complete in about 6–10 hours.

The catalyst or mixture of catalysts used in the reaction contains the elements copper, zinc and an alkaline earth metal. The catalyst may be supported or unsupported. Minor amounts of other metals may be present as long as they do not interfere with the catalytic action of the Cu-Zn-alkaline earth metal. The presence of any other catalytic metal is unnecessary. However, the presence of minor amounts of cobalt, chromium and/or nickel is not considered detrimental.

The copper may be in the form of copper metal, copper oxide or copper carbonate (e.g. malachite, $CuCO_3Cu(OH)_2$). The form in which the copper exists may vary during the reaction due to the environment in which the catalyst exists. The copper catalyst is preferably added in the form of copper oxide. Copper carbonate is believed to form copper oxide in the reaction. Partial reduction to a lower valence or to copper metal may occur, especially if the catalyst is contacted with hydrogen before and/or during the alkylation. However there is no indication of copper metal formation.

Zinc can be added as zinc metal powder or in the form of a zinc compound such as zinc oxide, zinc hydroxide, zinc carbonate, zinc acetate, zinc formate, zinc chloride, zinc sulfate, zinc phosphate and the like. Preferably the zinc is added in the form of zinc oxide.

Alkaline earth metal can be introduced in the form of an alkaline earth metal compound such as barium oxide, barium hydroxide, barium carbonate, barium sulfate, barium chloride, calcium oxide, calcium hydroxide, calcium carbonate, magnesium oxide, magnesium hydroxide, magnesium carbonate and the like including mixtures thereof. Preferably the alkaline earth metal is a basic compound. The most preferred alkaline earth metal is barium and is introduced in the form of a basic barium compound such as barium oxide, barium hydroxide, barium carbonate or mixtures thereof and the like. The most preferred form of barium is barium carbonate.

The catalytic metals can be introduced separately or as a single compound or mixture of compounds. That is the catalyst can be introduced by adding copper or a copper compound, zinc or a zinc compound and an alkaline earth metal base as three separate components. For example, the catalyst will form by adding copper oxide, zinc oxide and barium hydroxide separately to the reaction mixture.

Alternatively the copper, zinc and alkaline earth metal may be co-precipitated from a solution to form an intimate catalytic mixture. For example, copper nitrate, zinc nitrate and barium nitrate may be dissolved in aqueous nitric acid and precipitated so oxides and/or hydroxides by adding sodium hydroxide or carbonate to form an alkaline mixture. The co-precipitated mixture can be filtered to recover the solid catalyst, dried and crushed to form a fine powder which can be added to the reaction mixture as the catalyst.

Another way to form the catalyst is to impregnate a catalyst support with an aqueous solution of a water soluble salt of the catalytic metal. For example, an aqueous solution of copper nitrate, zinc nitrate and barium nitrate may be formed and used to impregnate a catalyst support such as alumina, silica, silica-alumina, magnesia, zirconia, kieselguhr, natural and synthetic zeolites and mixtures of the foregoing supports. The dry support is placed in the aqueous catalyst solution and allowed to absorb the solution. The remaining solution can be drained off or evaporated. The impregnated support is then dried and finally calcined at an elevated temperature, for example 400°–800° C. in the presence of air to form the active catalyst.

The atom ratio of copper to zinc to alkaline earth metal can vary widely. A useful range of catalytic metal is 10–100 copper: 10–100 zinc: 0.02–40 alkaline earth metal. More preferably the atom ratio is 10–30 copper: 10–30 zinc: 0.1–10 alkaline earth metal nd most preferably about 20:20:1.

The amount of catalyst in the reaction mixture should be a catalytic amount. This means an amount which will catalyze the reaction of the alcohol and amine to alkylate the amine. The amount of catalyst is expressed in terms of weight percent total catalytic metal based on the weight of the reaction mixture. A useful range of catalyst is about 0.001–25 weight percent. A more preferred amount of catalyst is 0.05–7 weight percent and a most preferred amount of catalyst is 1–5 weight percent.

Previous catalysts containing copper that have been used to catalyze the reaction of amines with alcohol suffered from the problem that the copper tends to dissolve in the reaction system and deposit throughout the reactor. This is readily apparent from the blue color of the reaction mixture. Surprisingly, it has been found that in the present catalyst system the copper does not appear to dissolve as shown by the lack of blue color in the liquid phase.

The catalyst can be recovered at the completion of the reaction by settling and/or filtration. Filtration is improved by including an inert filter aid such as Celite diatomaceous earth in the reaction mixture. Optionally the catalyst may be supported as previously described which makes separation much easier. The recovered catalyst can be recycled without further treatment and without noticeable loss of activity. If desired the catalyst may be dried prior to recycle.

The process can be used to alkylate the nitrogen atom of any primary or secondary amine. Examples of primary amines include methylamine, ethylamine, 1-propylamine, isobutylamine, 1-butylamine and the like. Preferred monoalkylamines are those in which the alkyl group contains about 1–8 carbon atoms and more preferably 1–4 carbonatoms, especially methylamine.

Examples of secondary amines include imethylamine, diethylamine, di-n-butyl amine, didecylamine, di(2-ethyl-decyl)amine, dioctadecylamine, methyl dodecylamine, methyl eicosylamine, methyl docosylamine, methyl triacontylamine, isobutyl 2-ethylhexyl amine, n-butyl hexadecylamine, ethyl nonylamine, ethyl tetradecylamine, methyl cyclohexylamine, ethyl cyclohexylamine, piperazine, piperidine, N-methyl aniline, N,N'-dimethyl phenylene diamine and the like. The preferred secondary amines are the di-lower alkylamines such as the di-$C_{1-4}$alkylamines. The most preferred secondary amines are di-$C_{1-4}$ alkylamines, especially dimethylamine ("DMA").

Any alcohol containing 1 to about 30 carbon atoms can be used. Representative examples of these alcohols include methanol, ethanol, isopropanol, n-propanol, isobutanol, n-butanol, 2-ethyl hexanol, n-octanol, n-decanol, n-dodecanol, 2-ethyldecyl alcohol, n-tetradecanol, n-hexadecanol, n-octadecanol, 2-ethylhexadecyl alcohol, n-eicosanol, n-docosanol, 2-ethyleicosyl alcohol, n-tetracosanol, n-triacontanol and the like.

The most useful alcohols are the $C_{8-22}$ mainly straight chain primary alcohols. By "mainly" is meant at least 80 mole percent.

The reaction is preferably conducted in the presence of hydrogen during at least a portion of the reaction. As mentioned earlier the hydrogen can be sparged into the reaction liquid phase together with the di-lower alkylamine (e.g., dimethylamine). The amount or rate of hydrogen sparge does not appear to be critical and indeed the alkylation will proceed without hydrogen sparge albeit at a slower rate. A useful hydrogen sparge rate is 0.001–1000 moles of hydrogen per hour per mole of alcohol.

The hydrogen sparge can be used intermittently or continuously during the alkylation. The hydrogen can be diluted with an inert gas such as nitrogen. In one embodiment, hydrogen or a mixture of hydrogen and nitrogen are injected at the start of the reaction to activate the catalyst and then the hydrogen stopped while the nitrogen sparge is started or continued to assist in water removal. If the reaction rate decreases additional hydrogen can be added to the di-lower alkylamine sparge either continuously or periodically to re-activate the catalyst.

An especially preferred embodiment of the invention is a process for making $C_{8-22}$ alkyl dimethylamine, said process comprising,
 (A) mixing a catalyst consisting essentially of a copper oxide, zinc oxide and an alkaline earth metal base with a $C_{8-22}$ primary mainly straight chain alcohol
 (B) contacting the mixture of alcohol and catalyst with hydrogen while heating to a reaction temperature of about 180°–250° C.
 (C) adding dimethylamine to the mixture of alcohol and catalyst while at said reaction temperature in an amount sufficient to convert at least 95 percent of said alcohol to $C_{8-22}$ alkyl dimethylamine and
 (D) recovering said $C_{8-22}$ alkyl dimethylamine.

Another especially preferred embodiment of the invention is a process for making a di-($C_{8-22}$ alkyl) methylamine, said process comprising:
 (A) mixing a catalyst consisting essentially of a copper oxide, zinc oxide and an alkaline earth metal base with a $C_{8-22}$ primary mainly straight chain alcohol
 (B) contacting the mixture of alcohol and catalyst with hydrogen while heating to a reaction temperature of about 180°–250° C.
 (C) adding methylamine to the mixture of alcohol and catalyst while at said reaction temperature in an amount sufficient t convert at least 95 percent of said alcohol to Di($C_{8-22}$ alkyl) methylamine and
 (D) recovering said Di($C_{8-22}$ alkyl) methylamine.

In these especially preferred embodiments the catalyst is mixed with the alcohol before the catalyst contacts the amine. The alcohol catalyst mixture is then heated rapidly to reaction temperature, about 180°–250° C., while contacting the mixture with hydrogen. This serves to activate the catalyst. Once in this activated state the amine reactant can be added without degrading the activity of the catalyst. Contact of the catalyst with amine prior to hydrogen activation has been observed to sharply curtail the reaction rate.

In an optional mode of operation the catalyst can be preactivated during manufacture and then added to the alcohol. The alcohol can be pre-heated to reaction temperature prior to catalyst addition or post-heated rapidly to reaction temperature. Amine feed is then commenced preferable with at least some hydrogen to maintain catalyst activity.

The following examples serve to show how the process is carried out and the results which are achieved.

EXAMPLE 1

In a reaction vessel was placed 100 grams of commercial grade n-dodecanol (EPAL®-12 alcohol, Ethyl Corporation), 1.0 grams CuO powder, 1.0 grams ZnO powder and 0.2 grams Ba(OH)$_2$·8H$_2$O. The vessel was then purged by sparging nitrogen into the liquid phase and allowing the excess nitrogen to vent. The reaction mixture was heated to 100° C. while stirring. Nitrogen sparge was stopped and hydrogen sparging was started at 0.8 SCFH. Heating was continued to 200° C. at which temperature hydrogen sparge was reduced to 0.4 SCFH and dimethylamine (DMA) feed in a gas state was started. Over a 4-hour period, 115 grams of DMA was fed at 202°–205° C. The vent gas (mainly hydrogen, unreacted DMA and volatiles) was passed through a condenser and condensate collected in a Dean Stark water trap forming a 2-phase condensate. The lower aqueous phase was removed and weighed 9.6 grams. After standing overnight, the mixture was again heated to 115° C. with nitrogen sparge and then nitrogen was shut off and hydrogen sparge commenced at 0.8 SCFH. Heating was continued up to 200° C. and DMA vapor feed again started while dropping the hydrogen sparge to 0.4 SCFH. DMA feed was continued for 3 hours through the water trap. An additional 1.6 grams of aqueous layer remove the catalyst giving 75.1 grams of filtrate. The filtrate was analyzed by gas chromatography (GC) as follows:

|  | Area Percent |
| --- | --- |
| dodecyl dimethylamine | 93.5 |
| dialkylmethylamine | 3.2 |
| dodecanol | 1.4 |

EXAMPLES 2-4

The above procedure was repeated with the following modifications:

| Example | Reaction Temp (°C.) | Reaction Time (Hrs) |
|---|---|---|
| 2 | 230 | 4 |
| 3 | 206 | 7 |
| 4 | 200 | 8 |

The product analyzed by GC (area percent) as follows:

|  | Example | | |
|---|---|---|---|
|  | 2 | 3 | 4 |
| dodecyl dimethylamine | 86.6 | 93.8 | 95.1 |
| dialkylmethylamine | 10.9 | 3.2 | 2.7 |
| dodecanol | 0.2 | 1.2 | 0.3 |

EXAMPLES 5-7

These examples show the process conducted with catalyst recycle. In each case the reactor charge was about 100 grams of n-dodecanol plus catalyst. Reaction time was 8 hours at 200°–204° C. with 140 grams of DMA feed (145 grams in Example 7) and hydrogen sparge at 0.4 SCFH. In Example 5 the catalyst charge was 1.0 gram ZnO, 1.0 gram CuO and 0.2 gram Ba(OH)$_2$·8H$_2$O.

In Example 6 the catalyst was 2.8 grams of filtered wet catalyst recovered from Example 5 plus 0.22 grams of fresh CuO—ZnO—Ba(OH)$_2$·8H$_2$O catalyst in the same metal ratio as before.

In Example 7 the catalyst was 1.7 grams of recovered wet catalyst from Example 6 and 0.22 grams of fresh CuO—ZnO—Ba(OH)$_2$·8H$_2$O catalyst.

The following table shows the result of the recycle runs in area percent by GC.

|  | Example | | |
|---|---|---|---|
|  | 5 | 6 | 7 |
| dodecyl dimethylamine | 95.7 | 96.4 | 96.2 |
| dialkylmethylamine | 2.6 | 2.2 | 2.4 |
| dodecanol | 0.2 | 0.2 | 0.2 |

Little, if any, copper migration was observed in the run. The examples demonstrate that the process is capable of giving very high conversion of alcohol to amines.

EXAMPLE 8

In a 2 liter reaction vessel was placed 940 grams of a commercial grade n-octadecanol(EPAL ®18 Alcohol, Ethyl Corporation), 10 grams of CuO powder, 10 grams of ZnO powder and 2.0 grams of Ba(OH)$_2$·8H$_2$O. The vessel was sparged with nitrogen and heated with stirring to 140° C. Nitrogen sparge was stopped and hydrogen sparge was commenced at 0.46 SCFH. Heating was continued and at 202° C. gaseous DMA was injected into the liquid phase together with the hydrogen sparge. Over a 10-hour period, 550 grams of DMA was fed at 216° C. Volatiles removed in the vent gas were condensed. The reaction mixture was cooled and filtered to remove the catalyst. The product analyzed by GC as follows:

|  | Area Percent |
|---|---|
| octadecenyl dimethylamine | 2.1 |
| octadecyl dimethylamine | 85.1 |
| dioctadecyl methylamine | 7.5 |
| octadecanol | 0.28 |
| other | 5.0 |

EXAMPLES 9-13

A series of tests was conducted without hydrogen sparge to measure the relative activity of several catalyst systems without attempting to achieve maximum conversion. In these tests an autoclave was charged with 100 grams of n-dodecanol and the indicated catalyst. Then 30 grams of DMA was added and the autoclave sealed and pressurized to 100 psig with hydrogen. Over a 30-minute period the autoclave was heated to 210° C. and then stirred at 210° C. for exactly four hours. The reaction mixture was then sampled and analyzed by GC. The results of Examples 9-13 are tabulated in the following table:

| Example | Catalyst | | Product (Area %) | |
|---|---|---|---|---|
|  |  | n-dodecanol | n-dodecyl dimethyl amine | n-dodecyl methyl amine |
| 9 | 1.0 g CuO, 0.1 g Cr$_2$O$_3$, 0.1 g BaO | 80.8 | 18.1 | 1.1 |
| 10 | 1.0 g CuO, 0.1 g Cr$_2$O$_3$, 0.1 g BaO, 1.0 g ZnO[2] | 66.9 | 29.7 | 2.3 |
| 11 | 1.0 g CuO, 0.1 g Cr$_2$O$_3$, 0.1 g BaO, 1.0 g ZnO | 73.3 | 22.7 | 1.1 |
| 12 | 1.0 g CuO, 1.0 g ZnO, 0.1 g Ba(OH)$_2$ | 93.3 | 6.0 | trace |
| 13 | 1.0 g ZnO | 99.5 | trace | — |

1. Each added separately
2. Recycled from Example 10

Comparing Examples 9 and 10 it can be seen that zinc oxide significantly increases the conversion to n-dodecyl dimethylamines from 18.1 percent up to 29.7 percent. Comparing Examples 10 and 12 it can be seen that the inclusion of $Cr_2O_3$ with the $CuO$—$ZnO$—$Ba(OH)_2$ increases the conversion to n-dodecyl dimethylamine while at the same time introducing a small amount of n-dodecyl methylamine which could be detrimental in some instances since it is difficult to separate this coproduct from n-dodecyl dimethylamine. However, where the presence of this coproduct is not detrimental the further inclusion of $Cr_2O_3$ promoter is advantageous when making a $C_{8-22}$ alkyl dimethylamine. Similar promoter effects are obtained by including cobalt and/or nickel preferably in the form of an oxide.

The following example shows the process conducted with magnesium carbonate as the alkaline earth metal base.

EXAMPLE 14

In a reactor was placed 100 g of a mixture of primary $C_{16}$ plus $C_{18}$ alcohols and a catalyst consisting of 1.0 g copper oxide, 1.0 g zinc oxide and 0.2 g magnesium carbonate. DMA and hydrogen were sparged into the vigorously stirred liquid phase at 210° C. The total amount of DMA fed was 140% of theoretical. Samples were removed every hour and analyzed as follows:

| Reaction Time (hrs) | Composition (Area %)[2] | |
|---|---|---|
| | Alcohol | Alkyl Dimethylamine[1] |
| 1 | 89.3 | 1.8 |
| 2 | 40.4 | 49.6 |
| 3 | 8.4 | 82.7 |
| 4 | 0.9 | 88.8 |

[1]$C_{16-18}$ alkyl dimethylamine.
[2]Balance is mixture of by-products.

EXAMPLE 15

This alkylation was conducted using barium carbonate as the alkaline earth metal base.

In a reactor was placed 1977 g mixed primary $C_{16}$–$C_{18}$ alcohol, 25 g copper oxide, 25 g zinc oxide and 5 g barium carbonate. DMA and hydrogen were sparged into the liquid phase over a 7.5-hour period at 210° C. Total DMA feed was 197% of theory.

The following table gives the results.

| Reaction Time (hrs) | Composition (Area %) | |
|---|---|---|
| | Alcohol | Alkyl Dimethylamine |
| 1 | 63.6 | 22.9 |
| 2 | 46.2 | 42.3 |
| 3 | 26.6 | 59.1 |
| 4 | 18.1 | 71.3 |
| 5 | 8.5 | 78.6 |
| 6 | 3.5 | 81.6 |
| 7.5 | 0.8 | 81.3 |

EXAMPLE 16

This reaction was conducted using the catalyst recovered from Example 15 by filtration and without hydrogen sparge.

In a reactor was placed 2030 g mixed $C_{16-18}$ primary alcohols and the catalyst recovered from Example 15. The reactor was sealed and DMA sparged into the liquid phase for 10 hours at 210° C. Total DMA feed was 111% of theory. The following table shows the composition of the alkylation mixture during the reaction.

| Reaction Time (hrs) | Composition (Area %) | |
|---|---|---|
| | Alcohol | Alkyl Dimethylamine |
| 1 | 70.4 | 20.2 |
| 2 | 53.8 | 36.4 |
| 3 | 43.0 | 46.6 |
| 4 | 30.9 | 58.6 |
| 5 | 21.4 | 63.9 |
| 8 | 8.7 | 74.9 |
| 9 | 3.5 | 78.1 |
| 10 | 1.9 | 79.3 |

These results show that it is not necessary to sparge hydrogen through the reaction mixture during the alkylation. The rate, however, is somewhat lower without the hydrogen sparge.

The following example shows the process conducted with a calcium base.

EXAMPLE 17

In a reaction vessel was placed 100 grams of commercial grade n-dodecanol (EPAL®-12 alcohol, Ethyl Corporation), 2.2 grams of mixed $CuO/ZnO/CaCO_3$ powders (weight ratio of $CuO/ZnO/CaCO_3 = 5/5/1$). The vessel was then purged by sparging nitrogen into the liquid phase and allowing the excess nitrogen to vent. The reaction mixture was heated to 103° C. while stirring. Nitrogen sparge was stopped and hydrogen sparging was started at 0.8 SCFH. Heating was continued to 206° C. at which temperature hydrogen sparge was reduced to 0.4 SCFH and DMA vapor feed was started. Over a 7-hour period, 100 grams of DMA was fed at 206°–216° C. The vent gas (mainly hydrogen, unreacted DMA and volatiles) was passed through a condenser and condensate collected in a clean stark trap forming a 2-phase condensate. The lower aqueous phase collected was 15.5 milliliters. The reaction mixture was cooled and filtered to remove the catalyst. The filtrate was analyzed by GC as follows:

| | Area Percent |
|---|---|
| dodecyl dimethylamine | 93.9 |
| dialkylmethylamine | 3.6 |
| dodecanol | 1.0 |

The following Examples 18–36 show the process conducted with a mono-lower alkylamine.

EXAMPLE 18

In a reaction vessel was placed 50 grams of commercial grade 1-decanol, 0.48 grams of copper oxide, 0.01 grams of zinc oxide and 0.01 grams of barium hydroxide. The mixture was sparged with nitrogen for 15 minutes and then with hydrogen. The mixture was heated to 200° C. and the hydrogen sparge replaced with combined hydrogen and monomethylamine (MMA) sparge at a rate of 5 cc/min each. This was continued for 7 hours. At 4 hours and at 7 hours the reaction mixture was analyzed by GC with the following results:

| | 4 Hrs | 7 Hrs |
|---|---|---|
| 1-decanol | 3.4% | 0% |
| decyl methylamine | 9.2% | 15.5% |
| decyl dimethylamine | 0.2% | 0.4% |
| didecyl methylamine | 80.5% | 81.5% |

|  | 4 Hrs | 7 Hrs |
|---|---|---|
| didecyl amine | 0.2% | 0.6% |
| decyl decanoate | 1.6% | 1.5% |
| decyl decenyl methylamine | 2.7% | 0.7% |
| tridecylamine | 0.3% | 0.3% |

The analyses shows that the yield of didecyl methylamine had plateaued because all of the 1-decanol had been consumed. Calculation showed that an additional 8.55 grams of 1-decanol was needed to convert the decyl methylamine to didecyl methylamine. This alcohol was added and the mixture reacted at 200° C. for about 3 hours with hydrogen and nitrogen sparge (5 cc/min each) but without additional MMA sparge. The mixture analyzed at the end of this additional reaction period as follows:

| decyl dimethylamine | 0.4% |
|---|---|
| didecyl methylamine | 96.2% |
| decyl decanoate | 1.5% |

EXAMPLE 19

In a 100 ml glass reaction vessel was placed 50 grams commercial grade octadecanol, 0.48 grams copper oxide, 0.01 grams zinc oxide and 0.01 grams barium hydroxide (anhydrous). This was sparged with $N_2$ for 15 minutes and then with $H_2$ at 10 cc/min while heating to 200° C. for 4 hours. Since octadecanol is a solid at room temperature hot water was used in the vent gas condenser so water was not condensed. The sparge was stopped and the reaction mixture analyzed by GC:

| octadecanol | 0.3% |
|---|---|
| dioctadecyl methylamine | 96.7% |
| unknown | 1.8%[1] |

[1]Tentatively identified as either dioctadecylamine or octadecyl octadecanoate.

This reaction came out almost perfect without the need to add more alcohol or MMA and conduct a second stage reaction.

The catalyst can be recovered by filtration following each operation and recycled to the next operation. An inert filter aid such as diatomaceous earth can be included when using an unsupported catalyst to make the filtration easier. The entire catalyst and filter aid can be recycled to the next operation.

The process has been described as a batch operation. It can be converted to a continuous process by placing the catalyst, preferably on a support, in a tubular reactor of sufficient volume to give the required catalyst contact time at the desired reaction rate and passing the alcohol down through the catalyst bed while passing a countercurrent flow of hydrogen and lower alkylamine up through the catalyst bed while maintaining the catalyst at reaction temperature.

A series of experiments was conducted in a similar manner to make didecyl methylamine from n-decanol and MMA. The procedure used was to flush the round bottom glass reaction flask with nitrogen and charge 100 g alcohol and catalyst. The flask had a stirrer set to run at 200 rpm and a 5° C. water condenser over a Dean Stark water trap. A sparge tube extended into the liquid phase. The system was first sparged with nitrogen for 15 minutes and then hydrogen at 1 SCFH with nitrogen sparge stopped. The alcohol-catalyst mixture was heated at 200° C. over 30 min. while continuing hydrogen sparge. Then MMA (1 SCFH) was mixed with the hydrogen sparge. Any water collected in the Dean Stark separator was removed. The composition of the flask was periodically monitored by G. C. The following table gives modifications made during the series and results:

| Ex. | Catalyst | (g) | Reaction Time (hrs.) | Conversion[2] | Yield[3] |
|---|---|---|---|---|---|
| 20[1] | CuO | 0.48 | 1 | 6.8 | 58.4 |
|  | ZnO | 0.01 | 4 | 49.4 | 92.7 |
|  | Ba(OH)$_2$ | 0.01 | 7 | 73.6 | 93.6 |
| 21 | Copper[4] | 1.0 | 2 | 88.9 | 84.0 |
|  | Zinc[4] | 1.0 | 4 | 93.0 | 87.1 |
|  | Ba(OH)$_2$ | 0.2 | 6 | 95.8 | 79.9 |
| 22[5] | CuO | 6.1 | 2 | 70.6 | 87.3 |
|  | ZnO | 6.1 | 4 | 91.6 | 86.9 |
|  | Ba(OH)$_2$ | 2.0 | 6 | 95.3 | 85.7 |
| 23 | CuO | 1.0 | 1 | 17.7 | 77.7 |
|  | ZnO | 1.0 | 3 | 41.9 | 90.8 |
|  | BaCl$_2$ | 0.25 | 6 | 60.4 | 90.1 |
| 24 | CuO | 1.0 | — | — | — |
|  | ZnO | 1.0 | 6 | 84.1 | 87.9 |
|  | BaSO$_4$ | 0.24 | — | — | — |
| 25[6] | CuO | 1.0 | 2 | 32.6 | 83.0 |
|  | ZnO | 1.0 | 3 | 50.5 | 84.2 |
|  | BaCO$_3$ | 0.2 | 4 | 57.2 | 77.8 |
| 26 | CuO | 1.0 | 2 | 77.0 | 85.7 |
|  | ZnO | 1.0 | 4 | 97.7 | 85.0 |
|  | MgCO$_3$ | 0.49 | 6 | 99.4 | 83.1 |
| 27 | CuO | 1.0 | 1 | 49.3 | 89.4 |
|  | ZnO | 1.0 | 3 | 88.1 | 86.6 |
|  | BaCO$_3$ | 0.2 | 6 | 100.0 | 83.0 |
| 28 | CuO | 1.0 | — | — | — |
|  | ZnO | 1.0 | 4 | 82.5 | 90.3 |
|  | MgO | 0.25 | 6 | 94.4 | 88.9 |
| 29 | CuO | 1.0 | 2 | 59.0 | 89.2 |
|  | ZnO | 1.0 | 4 | 86.9 | 89.2 |
|  | Calcium[4] | 0.14 | 6 | 96.6 | 89.4 |
| 30 | CuO | 1.0 | 2 | 51.0 | 86.8 |
|  | ZnO | 1.0 | 4 | 73.8 | 89.9 |
|  | SrCO$_3$ | 0.24 | 6 | 89.4 | 87.9 |
| 31 | CuO | 1.0 | — | — | — |
|  | ZnO | 1.0 | — | — | — |
|  | BaCO$_3$ | 0.2 | 6 | 93.5 | 92.4 |
| 32 | CuO | 1.0 | — | — | — |
|  | ZnO | 1.0 | — | — | — |
|  | BaCO$_3$ | 0.2 | 6 | 93.6 | 91.6 |
| 33 | CuO | 1.0 | — | — | — |
|  | ZnO | 1.0 | — | — | — |
|  | BaCO$_3$ | 0.2 | 6 | 93.7 | 92.0 |

[1]50 g n-decanol, no $H_2$ sparge.
[2]"Conversion" is the percent of the alcohol consumed.
[3]"Yield" is the percent of the "consumed" alcohol that formed didecyl methylamine, monodecyl methylamine or unsaturated didecyl methylamine.
[4]As the metal powder.
[5]610.3 g n-decanol, MMA sparge at 2 SCFH.
[6]MMA sparge at 5 cfh.

A series of experiments was conducted to show the detrimental affect of contacting the catalyst with amine below reaction temperature. The procedure was the same as used in Examples 20–33. The catalyst in each case was 1 g CuO, 1 g ZnO, 0.2 g BaCO$_3$.

In Example 34 a hydrogen sparge of 1 SCFH was maintained while heating the n-decanol catalyst mixture to 200° C. over 30 minutes. Then the sparge was changed to 1 SCFH hydrogen plus 1 SCFH MMA for a 6 hour reaction at 200° C.

In Example 35 the hydrogen sparge during heat-up to reaction temperature was replaced by 1 SCFH MMA sparge.

In Example 36 the hydrogen sparge during heat-up was changed to 0.5 SCFH hydrogen plus 0.5 SCFH MMA.

The following table shows the results after a 6 hour reaction period.

| Example | Conversion | Yield |
|---------|-----------|-------|
| 34 | 93.6 | 91.6 |
| 35 | 53.0 | 92.8 |
| 36 | 64.2 | 94.0 |

Example 34 shows a typical baseline run with this catalyst. Example 35 shows the sharp drop in conversion caused by contact of the catalyst with amine during heat-up to reaction temperature. Example 36 shows that inclusion of hydrogen sparge with the premature amine contact can lessen the detrimental effect but does not entirely counteract the affect.

One of the most surprising features of the invention is that the catalytic components can be added separately and need not be added as a composite. It is not apparent how each component can cooperate with the other components to give the improved catalytic properties. This is especially applicable to the zinc or zinc oxide. Zinc oxide itself has little if any catalytic effect on the alkylation of amines by alcohols. This can be seen in above Example 13. However when zinc oxide is added to a copper-containing catalyst it greatly improves the effectiveness of the copper-containing catalyst. The zinc oxide can be mixed with the copper-containing catalyst and the mixture added to the reaction vessel or the zinc oxide can be separately added to the reaction vessel. For example copper oxide can be added to a reaction vessel containing the alcohol alkylating agent and the zinc oxide and barium hydroxide or carbonate added separately to the same reaction vessel. Alternatively copper oxide can be mixed with zinc oxide and barium hydroxide or carbonate and the mixture added to the reaction vessel. In another mode of operation the copper, zinc and barium may be impregnated on a suitable support either all at once from a common solution or separately from different solutions. Alternatively the copper, zinc and alkaline earth metal compounds (e.g., nitrates, acetates) may be dissolved in an aqueous solution and then mixed with base (e.g., $Na_2CO_3$, NaOH) to co-precipitate the catalyst.

From the above it can be seen that a further embodiment of the invention is an improvement in a process for making a trialkylamine by reacting an alkylamine selected from mono- and di-lower alkylamines in the liquid phase with a $C_{8-22}$ primary alcohol or mixtures thereof in the presence of a copper-containing catalyst. The improvement comprises adding zinc oxide to the reaction mixture. Results are improved still further by including an alkaline earth metal base, especially barium oxide, hydroxide carbonate or mixtures thereof in the reaction mixture. The improved process is preferably conducted in contact with hydrogen at least part time.

Another embodiment of the invention is the catalyst used in the process. This is a non-colloidal catalyst consisting essentially of supported or unsupported copper oxide, zinc oxide and an alkaline earth metal base. The base can be a barium, calcium or magnesium base such as an oxide, hydroxide or carbonate. The preferred alkaline earth metal base is barium hydroxide or barium carbonate. The atom ratio of copper:zinc:alkaline earth metal is preferably 10–30 copper:10–100 zinc:0.1–10 alkaline earth metal. A more preferred ratio is 10–30, copper:10–30 zinc:0.1–10 alkaline earth metal.

The preferred alcohol alkylating agents are the $C_{8-22}$ mainly straight-chain alpha-alcohols. By "mainly straight-chain" is meant that the alcohol is at least 80 mole percent straight-chain. One of the surprising features of the reaction that has been observed is that if a minor amount of a branched-chain alcohol is present in the alcohol reactant, it is apparently converted to straight-chain alcohol. This is based on the observation that the alkylation of dimethylamine with a commercial dodecanol which contained about 5 mole percent of branched alcohol yielded dodecyl dimethylamine in which the dodecyl groups were all straight-chain. The residual alcohol was analyzed by GC and branched-chain alcohol was not detected in the residue. Spiking the residue with a trace of branched-chain dodecanol and further analysis verified that the analytical method was capable of detecting branched-chain alcohol. The fate of the branched-chain alcohol is not known with certainty but it appears that it may be isomerized to form straight-chain alcohol.

We claim:

1. A non-colloidal catalyst suitable for catalyzing the reaction of a mono- or di-lower alkylamine with an alkanol thereby alkylating said amine, said catalyst consisting essentially of supported or unsupported copper oxide, zinc oxide, and an alkaline earth metal base selected from the group consisting of barium oxide, barium hydroxide, barium carbonate, calcium hydroxide, calcium carbonate, magnesium hydroxide, magnesium carbonate, and mixtures thereof.

2. A non-colloidal catalyst of claim 1 wherein said alkaline earth metal base is barium oxide, barium hydroxide, barium carbonate or mixtures thereof.

3. A non-colloidal catalyst of claim 2 wherein said alkaline earth metal base is barium carbonate.

4. The catalyst of claim 1 having the components in the atomic ratios 10–100 Cu/10–100 Zn/0.02–40 alkaline earth metal.

5. The catalyst of claim 4 having the components in the atomic ratios 10–30 Cu/10–30 Zn/0.1–10 alkaline earth metal.

6. The catalyst of claim 5 having the components in the atomic ratios 20 Cu/20 Zn/1 alkaline earth metal.

7. The catalyst of claim 2 having the components in the atomic ratios 10–100 Cu/10–100 Zn/0.02–40 Ba.

8. The catalyst of claim 7 having the components in the atomic ratios 10–30 Cu/10–30 Zn/0.1–10 Ba.

9. The catalyst of claim 8 having the components in the atomic ratios 20 Cu/20 Zn/1 Ba.

10. The catalyst of claim 3 having the components in the atomic ratios 10–100 Cu/10–100 Zn/0.02–40 Ba.

11. The catalyst of claim 10 having the components in the atomic ratios 10–30 Cu/10–30 Zn/0.1–10 Ba.

12. The catalyst of claim 11 having the components in the atomic ratios 20 Cu/20 Zn/1 Ba.

* * * * *